US011371969B2

(12) United States Patent
Bonda

(10) Patent No.: US 11,371,969 B2
(45) Date of Patent: Jun. 28, 2022

(54) GAS-ANALYSIS SAMPLE INJECTION SYSTEM AND METHOD

(71) Applicant: Joseph Bonda, New Orleans, LA (US)

(72) Inventor: Joseph Bonda, New Orleans, LA (US)

(73) Assignee: Joseph George Bonda, New Orleans, LA (US)

( * ) Notice: Subject to any disclaimer, the term of this patent is extended or adjusted under 35 U.S.C. 154(b) by 260 days.

(21) Appl. No.: 16/725,260

(22) Filed: Dec. 23, 2019

(65) Prior Publication Data

US 2021/0190735 A1 Jun. 24, 2021

(51) Int. Cl.
*G01N 30/32* (2006.01)
*G01N 30/24* (2006.01)
*G01N 30/02* (2006.01)

(52) U.S. Cl.
CPC ............ *G01N 30/24* (2013.01); *G01N 30/32* (2013.01); *G01N 2030/025* (2013.01); *G01N 2030/328* (2013.01)

(58) Field of Classification Search
CPC .. G01N 30/24; G01N 30/32; G01N 2030/328; G01N 2030/025; G01N 1/22
USPC .......... 73/23.41, 23.34, 863, 863.01, 863.31, 73/863.33, 864.81, 864.8, 3, 864.84; 422/83, 89
See application file for complete search history.

(56) References Cited

U.S. PATENT DOCUMENTS

| | | | |
|---|---|---|---|
| 3,255,594 A | 6/1966 | Mayfield | |
| 3,841,160 A | 10/1974 | Iwao | |
| 3,842,679 A | 10/1974 | Iwao et al. | |
| 4,120,662 A | 10/1978 | Fosslien | |
| 4,311,484 A | 1/1982 | Fosslien | |
| 4,402,910 A * | 9/1983 | Smith | F24T 10/30 422/83 |
| 5,205,177 A * | 4/1993 | DuBrock, Jr. | G01N 1/2258 73/863.12 |
| 5,600,075 A * | 2/1997 | Peterson | G01N 1/22 73/863.71 |
| 5,918,290 A | 6/1999 | Auck | |
| 7,162,933 B2 | 1/2007 | Thompson et al. | |
| 9,562,833 B2 | 2/2017 | Thompson et al. | |
| 10,161,851 B2 | 12/2018 | Scipolo et al. | |
| 2015/0000426 A1 | 1/2015 | Rolston et al. | |

* cited by examiner

*Primary Examiner* — Robert R Raevis

(57) ABSTRACT

A gas-analysis sample injection system and method for transfer of sample gas from a gas-sample cylinder to an analyzer such as a gas chromatograph, providing a cabinet with a door and a cabinet vent, vent manifold, and vent exhaust, a carrier gas supply, a sample cylinder support bracket, a sample filter housing, and a sample injector valve with an injector-valve actuator. Controlled by a valve controller over valve-control lines, a carrier gas regulating valve and sample-cylinder inflow valve allow carrier gas at regulated pressure into the mounted gas-sample cylinder, and a sample-cylinder outflow valve and sample transfer valve allow flow of sample gas into the sample injector valve. A filter vent valve and injector-valve vent valve operate in coordination with the other valves to provide venting and purging of extraneous gasses.

9 Claims, 12 Drawing Sheets

GAS-ANALYSIS SAMPLE INJECTION SYSTEM AND METHOD

BACKGROUND OF THE INVENTION

This invention provides a gas-analysis sample injection system and method for transfer of sample gas from a gas-sample cylinder to an analyzer such as a gas chromatograph.

Gasses, such as natural gas, are analyzed for a variety of reasons, including testing which must be done before a unit of gas can be transported in a pipeline. Gas chromatography is a usual method of analysis. Standard gas-sample cylinders are known for the collecting and transporting of samples of gasses. An inert carrier gas is added to the sample gas and a known amount of the sample gas, calibrated as to pressure and volume, is introduced into the gas chromatograph or other analyzer. The process of transferring a sample of gas from the gas-sample cylinder to the analyzer can have problems such as leakage of some of the gas into the environment and contamination of the gas sample with extraneous gasses, substances, or air. Leakage of sample gas into the environment can be hazardous to persons performing the transfer and analysis operations. Presently, sometimes a type of snorkel is provided to draw away the air, including any contaminants, above the analyzer and transfer equipment. But that method is not very effective, especially for heavier-than-air gasses. Sometimes operations are performed inside a vented hood, but such vented hoods are expensive to install and operate, and the limited space inside such hoods is not best utilized with a permanent installation of bulky equipment. Sample cabinets presently known are subject to deficiencies and inefficiencies which either provide too little safety for personnel and equipment, or are too cumbersome and expensive, or have other problems.

What is needed is a gas-analysis sample injection system providing reliable venting that removes extraneous gasses before the testing at hand is performed, and removes any extraneous gasses released during the testing at hand, to avoid contaminating the next test, providing calibrated and repeatable sample transfer, providing a high level of reliable automation of transfer procedures, and above all providing for the safety of personnel and equipment, in a reasonably sized, straightforward-to-operate unit.

U.S. Pat. No. 5,918,290 for a "Multi-Product Sampling Apparatus and Method," issued on Jun. 29, 1999 to inventor Rodney D. Auck, provides for a multi-product sampling mechanism having a clean valve, a sample cabinet connected to the clean valve, and a utility cabinet connected to the clean valve and the sample cabinet for controlling and cleaning the operation of the clean valve and the sample cabinet. In a preferred embodiment, the sample cabinet includes connection blanks for the connection of additional sample cabinets so that, if desired, more than one particular type of product or chemical can be received exclusively at a designated sample cabinet. Additionally, in a preferred embodiment, the clean valve is connected a spacer connection for connecting the clean valve to a bulk-storage tank at the receiving facility. The spacer connection is also connected to the utility cabinet. By means of the use of connecting tubing, cleansing fluid such as ultra-pure water is utilized to operate a spray gun and inert gas such as nitrogen is utilized to operate the pneumatic valves, as well as for use of UPW followed by nitrogen gas to purge the connection tubing. As a result, the multi-product sampler is capable of being automatically cleaned and ready for receipt of product after use. Further, the collection of a chemical sample is accomplished in a safe, sealed area and cleansing fluids and gases and chemicals flushed or spilled are directed to appropriate environmentally sensitive industrial waste or drum recovery facilities.

U.S. Pat. No. 10,161,851 for a "System and Method for Analyzing Dusty Industrial Off-Gas Chemistry," issued on Dec. 25, 2018 to inventors Vittorio Scipolo et al., provides for an off-gas analyzer for analyzing $H_2O$ vapor, CO, $O_2$, $CO_2$, and/or $H_2$ in a furnace gas stream that is fluidically coupled to a gas extraction probe. The analyzer includes an optical measurement cell having multiple sampling chambers, optically coupled to a laser. The analyzer measuring cell is housed within a heated cabinet having a heater operable to heat the interior thereof so as to maintain the extracted gas sample therein at a temperature about the condensation point of water. The analyzer allows for the analysis of the gas water vapor of wet off-gas samples.

U.S. Pat. No. 3,841,160 for an "Automatic Sampler Apparatus," issued on Oct. 15, 1974 to inventor Kumiry Roy Iwao, provides for a system for injecting sample fluids into an analyzer and processing the analysis data. The system comprises a fluid sample analyzer, a sample storage module for a number of fluid samples, an injection module by which samples are injected into the analyzer, a data recording or processing device, and a control module for governing the sequencing the operation of the system. The storage module houses a plurality of sample containing trays which can be loaded with samples remote from the system. A gas operated purging system is employed for minimizing the quantity of residual material injected into the analyzer with successive samples.

U.S. Pat. No. 3,842,679 for an "Automatic Sampler Apparatus of Modular Construction," issued on Oct. 22, 1974 to inventors Kumiry Roy Iwao et al., provides for a system for injecting sample fluids into an analyzer and processing the analysis data. The system comprises a fluid sample analyzer, a sample storage module for a number of fluid samples, an injection module by which samples are injected into the analyzer, a data recording or processing device, and a control module for governing and sequencing the operation of the system. The injection module and the storage module are configured to permit alternate orientations to facilitate horizontal or vertical injection without disconnecting of interconnecting conduits.

U.S. Pat. No. 3,255,594 for a "Method and Apparatus for Determining the Composition of a Liquefied Gaseous Mixture," issued on Jun. 14, 1966 to inventor Ivan B. Mayfield, provides for a method and apparatus for determining a criterion of the composition of a volatile mixture comprising a major portion of a normally gaseous constituent and a minor portion of a less volatile constituent wherein said liquid mixture is introduced into a first vaporization zone at a constant rate vaporizing a portion of said liquid and concomitantly cooling remaining liquid, said cooled remaining liquid is passed to a second vaporization zone evaporating all but a minor residue of said remaining liquid, said minor residue is continuously withdrawn, and the temperature of said minor residue withdrawn from second vaporization zone is measured.

U.S. Pat. No. 4,311,484 for a "Specimen Sampling Apparatus," issued on Jan. 19, 1982 to inventor Egil Fosslien, provides for a method of and apparatus for obtaining a sample from a specimen of blood or the like in a closed container at a first pressure and for delivering the sample to an analyzer for analysis. The apparatus comprises a hollow needle for penetrating the closed container movable from a retracted position to an extended position in which it penetrates the container for drawing a specimen sample therefrom, and back to its retracted position. A conduit connects the needle and the analyzer for delivery of a specimen sample to the latter. An aspirator reduces the pressure in this conduit to a pressure less than the aforesaid first pressure when the needle is in its extended position, a specimen sample thereby being aspirated from the container into the conduit for delivery to the analyzer. The apparatus is responsive to this aspiration to initiate transfer of the specimen sample from the conduit into the analyzer. The pressure in the conduit is at least equal to the first pressure following aspiration, thereby enabling the specimen sample readily to be drawn into the analyzer.

U.S. Pat. No. 4,120,662 for a "Specimen Sampling Apparatus," issued on Oct. 17, 1978 to inventor Egil Fosslien, provides for an apparatus for obtaining samples from specimens of blood or the like contained in a series of closed containers, which specimens include a plurality of particles such as cells. A pair of parallel feed screws moves the closed containers along a predetermined path to a sampling station and in one mode, a mixing mode, imparts motion to the closed containers while they are moved along the path to obtain a substantially uniform distribution of the particles contained therein. The apparatus includes a needle which penetrates the closed containers when they reach the sampling station to withdraw specimen samples from the containers. The apparatus includes a controller for tilting each closed container at the sampling station so that one end of the container is lower than the other end. The needle penetrates the lower end of the container.

U.S. Pat. No. 9,562,833 for a "Composite Gas Sampling System," issued on Feb. 7, 2017 to inventors Kenneth O. Thompson et al., provides for a sampling system for collecting periodic composite and/or non-composite samples of vaporized gas during a transfer process from a vaporizer of a cryogenic hydrocarbon liquid, and includes a direct sample pathway to a gas analyzer for instantaneous, real-time vaporized gas analysis; a speed loop pathway for directly collecting fresh vaporized gas samples for subsequent analysis; and a composite sample pathway including a pressurized sample accumulator for collecting a plurality periodically obtained samples of a select volume during the transfer process to create a composite sample of the vaporized gas.

SUMMARY OF THE INVENTION

This invention provides a gas-analysis sample injection system and method for transfer of sample gas from a gas-sample cylinder to an analyzer such as a gas chromatograph.

The gas-analysis sample injection system and method provide a cabinet with a door and a cabinet vent, vent manifold, and vent exhaust, a carrier gas supply, a sample cylinder support bracket, a sample filter housing, and a sample injector valve with an injector-valve actuator. Controlled by a valve controller over valve-control lines, a carrier gas regulating valve and sample-cylinder inflow valve allow carrier gas at regulated pressure into the mounted gas-sample cylinder, and a sample-cylinder outflow valve and sample transfer valve allow flow of sample gas into the sample injector valve. A filter vent valve and injector-valve vent valve operate in coordination with the other valves to provide venting and purging of extraneous gasses.

BRIEF DESCRIPTION OF THE DRAWINGS

Reference will now be made to the drawings, wherein like parts are designated by like numerals, and wherein.

DETAILED DESCRIPTION OF THE INVENTION

Figure 1:
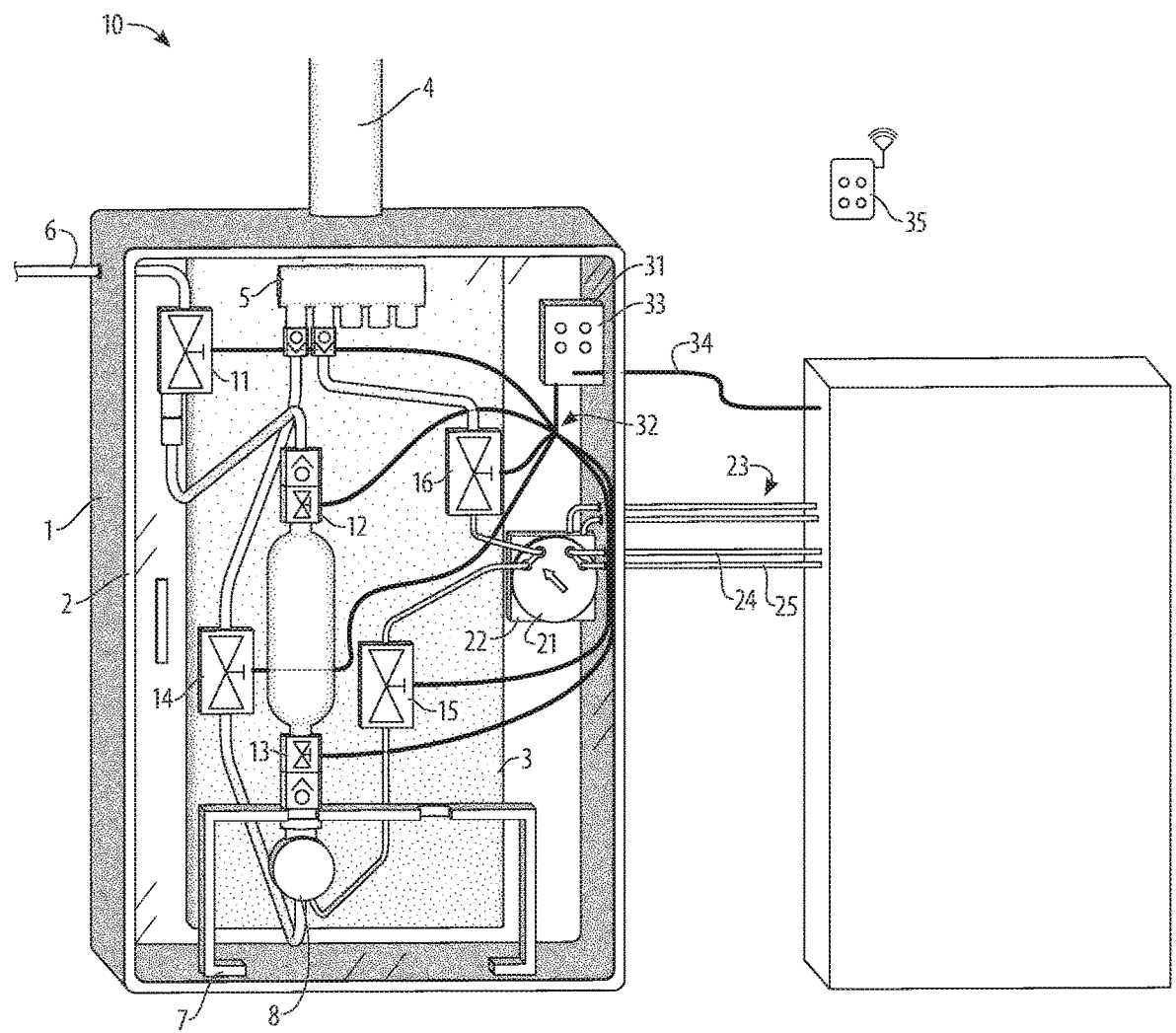
FIG. 1 is a schematic overview of the gas-analysis sample injection system of the invention in use with a gas chromatograph unit.

Referring to FIG. 1, the gas-analysis sample injection system 10 of the invention is shown. The gas-analysis sample injection system provides for transfer of sample gas from a gas-sample cylinder to an analyzer. A standard analyzer, most often a gas chromatograph, will provide signals to open and close a standard sample injector valve 21 with a standard injector-valve actuator 22. Although such a signal might be only a command to open or close the valve, often the analyzer also provides the motive force for the actuator, such as differential hydraulic, pneumatic, or electrical pressure over a pair of tubes or wires, as shown. A standard analyzer will also usually provide a flow of carrier gas over a sample-injection inflow line 24 in order to push the gas sample out of the sample injector valve 21 and into the analyzer over a sample-injection outflow line 25, as shown.

The gas-analysis sample injection system 10 provides for the temporary mounting of a standard gas-sample cylinder on a sample cylinder support bracket 7 inside a cabinet 1 having a door 2, providing an enclosure sealed against the escape of emitted gasses. The interior of the cabinet 1, when the door 2 is closed, is under a small negative air pressure, with a cabinet vent 3 and a vent exhaust 4 drawing any emitted gasses out of the enclosure and into, usually, the specialized environmental control exhaust system of the laboratory or other structure. The gas-analysis sample injection system 10 will likely be placed close to the analyzer in order to minimize the length of tubing between them. But, where appropriate, the gas-analysis sample injection system 10 can be placed at a greater distance from the analyzer, in another room, or on the other side of a partition, as might be appropriate when testing especially explosive or toxic substances. The illustrated embodiment, accommodating one or two standard-size gas-sample cylinders, is of a size very approximately one meter high, and can be placed on a lab bench near the analyzer. For very large-sized gas-sample cylinders, or a large number of standard cylinders, a larger or a floor-standing embodiment might be appropriate. For testing of potentially highly explosive substances, an embodiment having a reinforced cabinet 1 and door 2 might be appropriate.

The gas-analysis sample injection system 10 provides a carrier-gas supply 6 bringing a carrier gas under pressure into the enclosure. The carrier gas might be helium, nitrogen, argon, hydrogen, or filtered air, and might involve switching among carrier gasses for different tests.

In overview, the gas-analysis sample injection system 10 provides for the injection of a carrier gas into a mounted gas-sample cylinder, the flow of sample gas out of the gas-sample cylinder through a sample filter housing 8 containing a replaceable or rechargeable filter into the sample injector valve 21, and the transfer of a controlled amount of sample gas from the sample injector valve 21 to the analyzer for testing. The gas-analysis sample injection system 10 also provides for the venting of the lines and filter used for the transfer of the sample gas in order to prevent a current test being contaminated with trapped gasses from a prior test, and in order to carry away any leaked gasses that might otherwise linger in the enclosure and escape into the environment when the door 2 is opened by an operator. The sequence of opening and closing several valves 11, 12, 13, 14, 15, 16 is controlled by a valve controller 31 communicating with the valves over valve-control lines 32. Functions of each valve are treated in detail below. In a preferred embodiment, the valve controller 31 is based on a computer or microprocessor, with electrical signals on the valve-control lines 32 actuating servo motors incorporated into the valves.

A control panel 33 is provided for an operator to interact with the valve controller 31 such as activating the system after mounting a gas-sample cylinder and being informed of the status and completion of operations. The control panel 33 can be placed on the valve controller 31 inside the cabinet 1 as shown, or can be brought to the outside of the cabinet 1 or the door 2. In an optional embodiment, an analyzer communication line 34 can be connected between the valve controller 31 and the analyzer, under circumstances where the analyzer is equipped for such communication. In another optional embodiment, a controller remote-command unit 35 can be provided to allow remote control of the gas-analysis sample injection system 10. Such a controller remote-command unit 35 can use the known methods of wireless communication such as infrared or radio frequency methods, taking care not to introduce signals that might disrupt the operation of other laboratory equipment.

Figure 2:
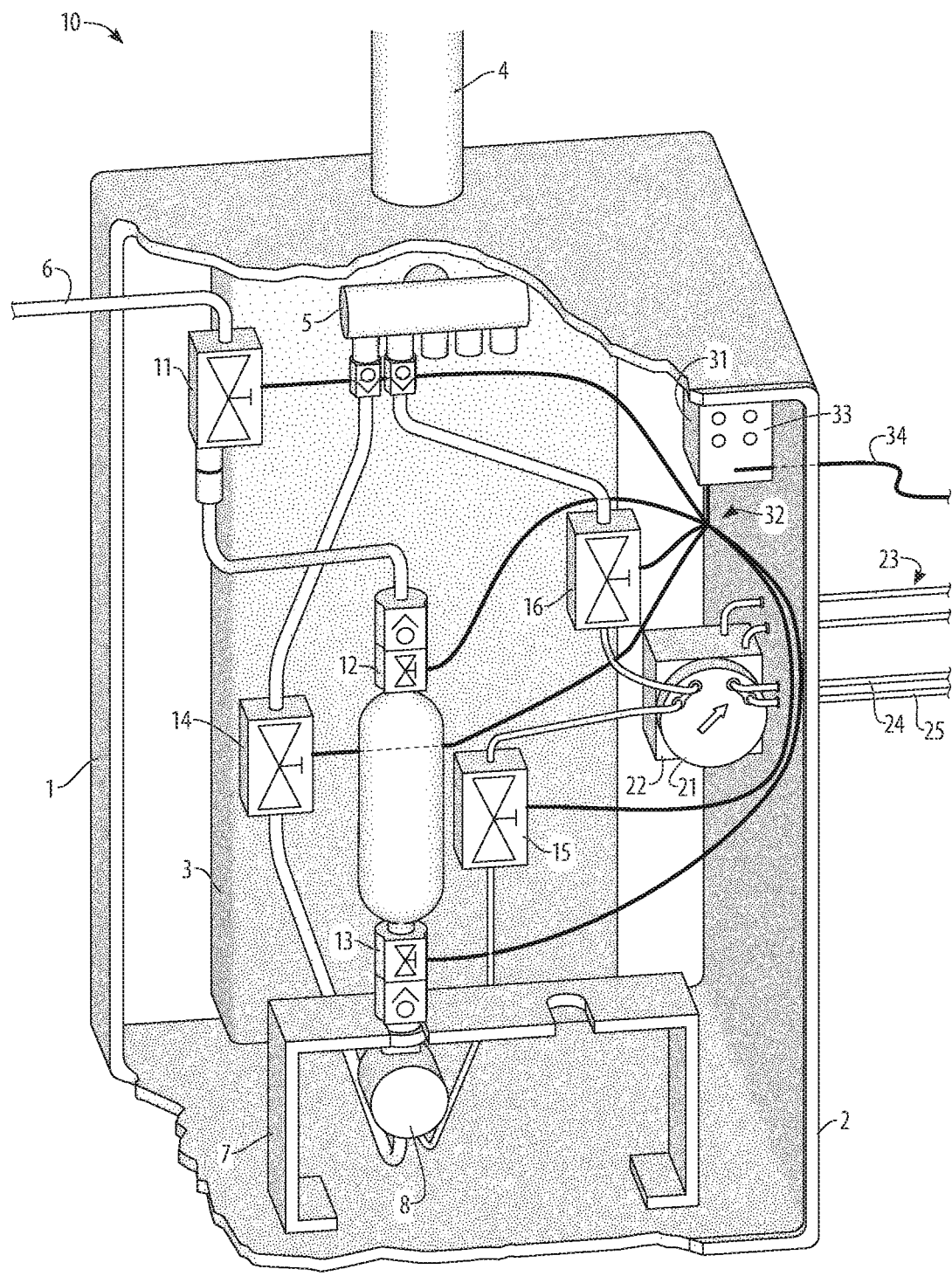
FIG. 2 is a cutaway view of the gas-analysis sample injection system of the invention.

Referring to FIG. 2, the filter vent valve 14 and the sample transfer valve 15 provide for the venting of the sample filter housing 8 and the sample injector valve 21 in order to ensure that any trapped contaminating gas left over from prior testing is eliminated. The filter vent valve 14 and the sample transfer valve 15 are connected by hoses or tubes to a vent manifold 5 that in turn feeds into the cabinet vent 3 and the vent exhaust 4. In a preferred embodiment, the vent manifold 5 provides quick connectors for the attachment of the hoses. As shown, the connections to the vent manifold 5 can be configured as check valves or one-way valves in order to prevent intrusion of gasses in unusual circumstances of reverse flow in the cabinet vent 3.

Figure 3:
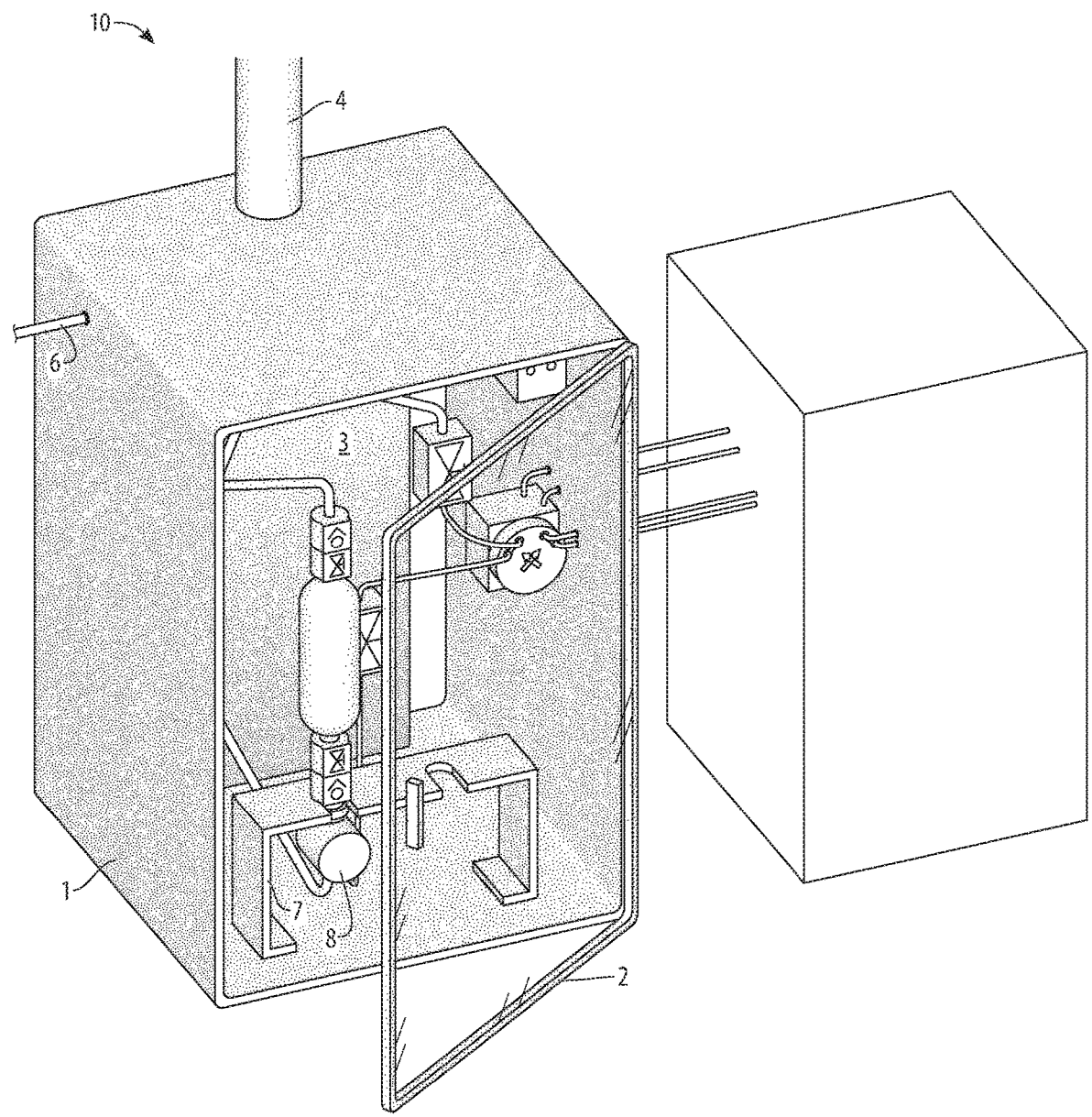
FIG. 3 is a perspective view of the gas-analysis sample injection system of the invention in use with the door open.

Referring to FIG. 3, a door 2 to the cabinet 1 is provided, which can be opened to allow the mounting or removal of gas-sample cylinders, and which seals against the escape of emitted gasses when closed. The door 2 also protects operators from injury in the event of an accident such as an explosive failure of a gas-sample cylinder or of a connection. Even when the door 2 is open, the cabinet 1 is subject to a negative air pressure from the cabinet vent 3 and vent exhaust 4.

Figure 4:
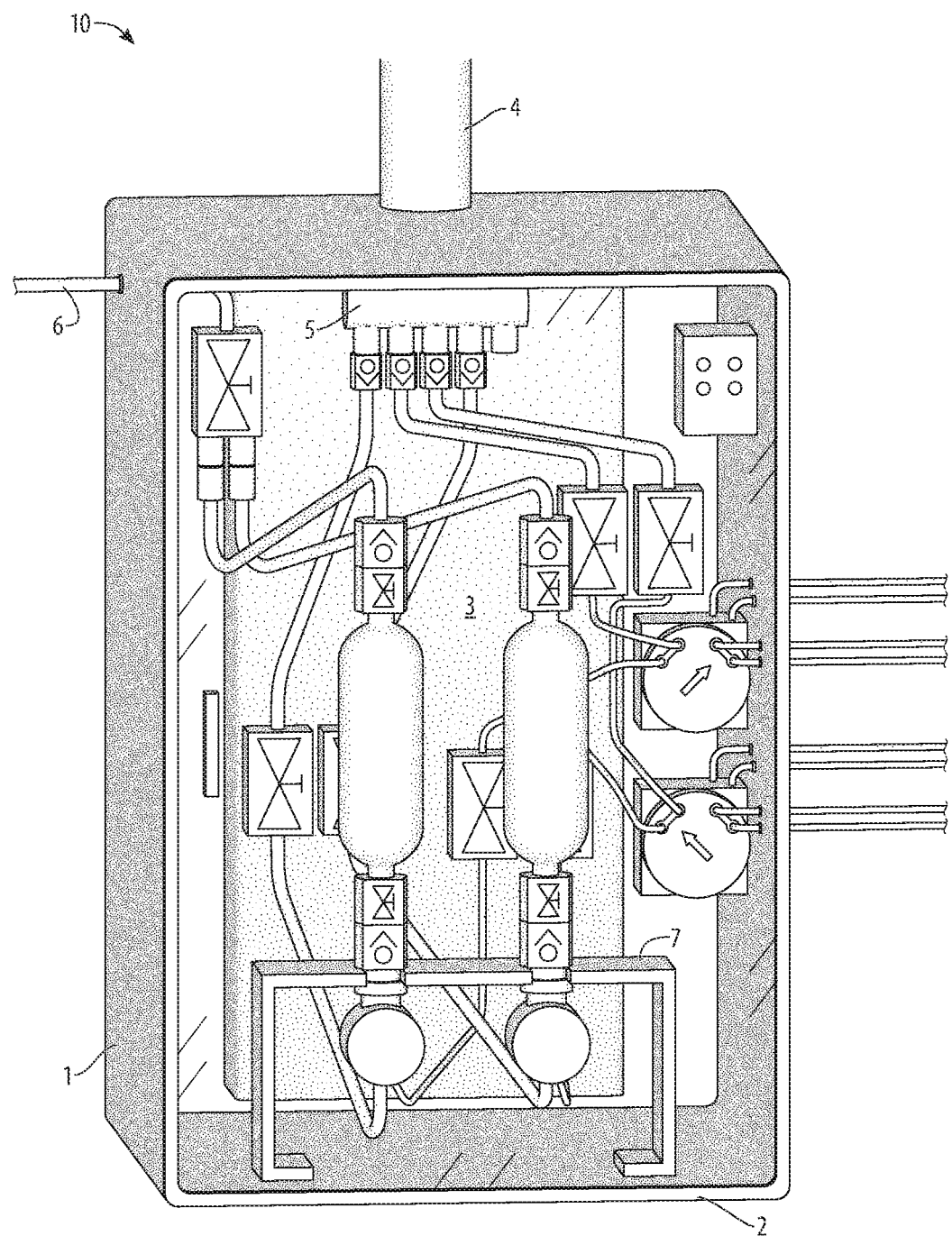
FIG. 4 is a schematic view of the gas-analysis sample injection system of the invention in use with two gas-sample cylinders.

Referring to FIG. 4, in a preferred embodiment, the gas-analysis sample injection system 10 provides for the simultaneous mounting of more than one gas-sample cylinder. In the embodiment shown, the sample cylinder support bracket 7 allows mounting of two gas-sample cylinders and the vent manifold 5 provides quick connections for the required four hoses plus another quick connection for a possible special need. This embodiment can supply two different analyzers or can supply an analyzer requiring two inputs. Embodiments able to accommodate more than two gas-sample cylinders are possible. The use of embodiments accommodating more than one gas-sample cylinder can provide a significant saving of bench space or floor space in a laboratory and alleviate the need for multiple connections to a venting or environmental control system and to a supply of carrier gas.

Figure 5:
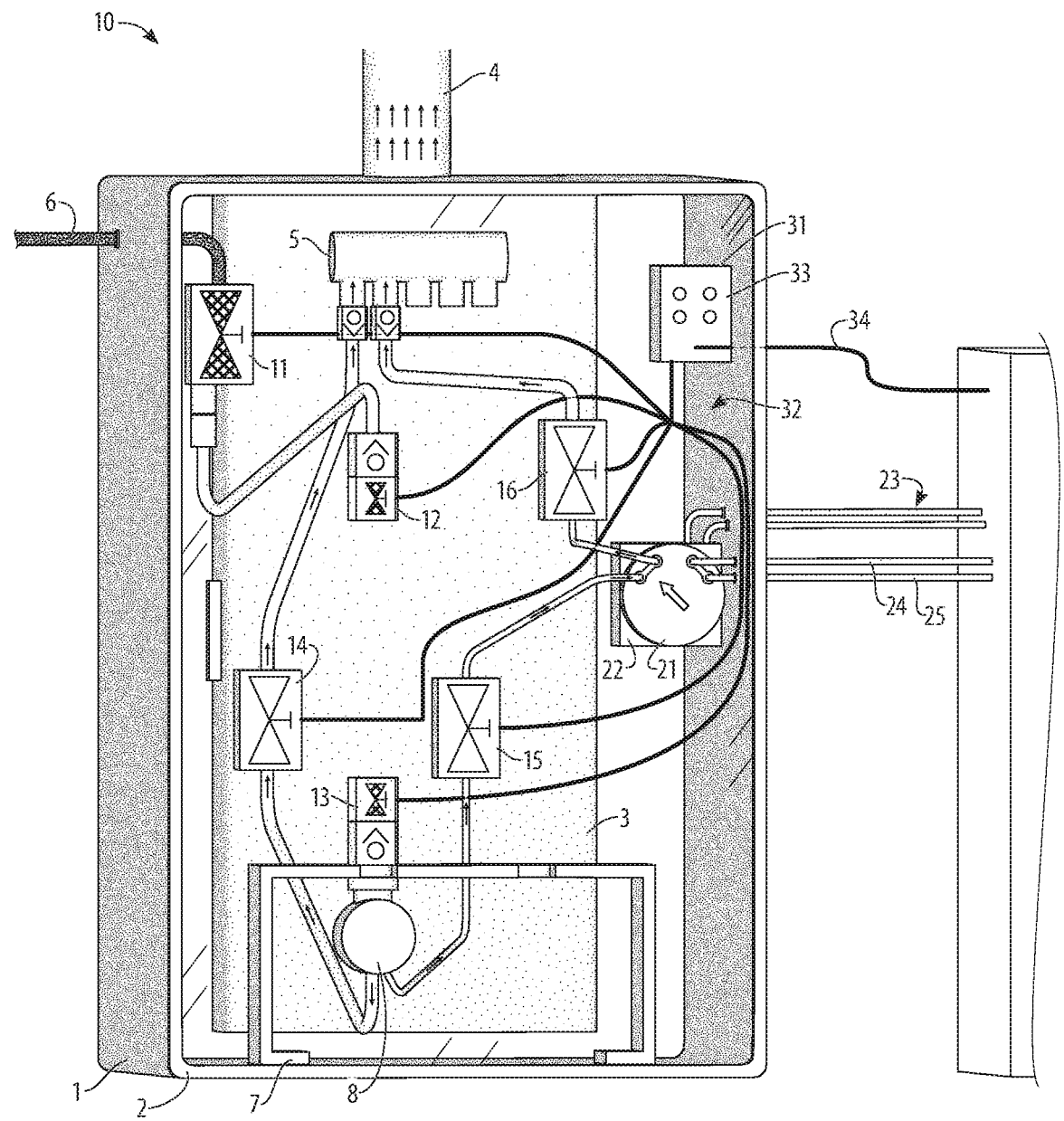
FIG. 5 is a schematic view of the gas-analysis sample injection system of the invention in use before a gas-sample cylinder is mounted.

Referring to FIG. 5, in use, at rest, with no gas-sample cylinder mounted, the carrier gas regulating valve 11 is closed, blocking the flow from the carrier-gas supply 6. Both the sample-cylinder inflow valve 12 and the sample-cylinder outflow valve 13 are closed, preventing entry or exit of air or extraneous gasses. As shown, the sample-cylinder inflow valve 12 and sample-cylinder outflow valve 13 can be configured as check valves or one-way valves in order to further ensure against intrusion of air or extraneous gasses. The filter vent valve 14 is open, so that the negative pressure of the cabinet vent 3 is applied to the sample filter housing 8 in order to draw away any extraneous gasses. The sample injector valve 21 is of a standard design where, in a closed position as shown, sample gas can enter the valve, pass through an internal chamber of calibrated size, and then exit the valve. When the sample injector valve 21 is moved to an open position by the injector-valve actuator 22, the internal chamber of the valve is moved into a position in line with the sample-injection inflow line 24 and sample-injection outflow line 25, resulting in the delivery of a calibrated amount of sample gas into the analyzer. With the gas-analysis sample injection system 10 at rest, and the sample injector valve 21 closed, as shown, the tubing path between the open sample transfer valve 15 and the open injector-valve vent valve 16 is continuous and connected, and the negative pressure of the cabinet vent 3 is applied through the sample injector valve 21 and down to the sample filter housing 8, in order to draw away any extraneous gasses.

Figure 6:
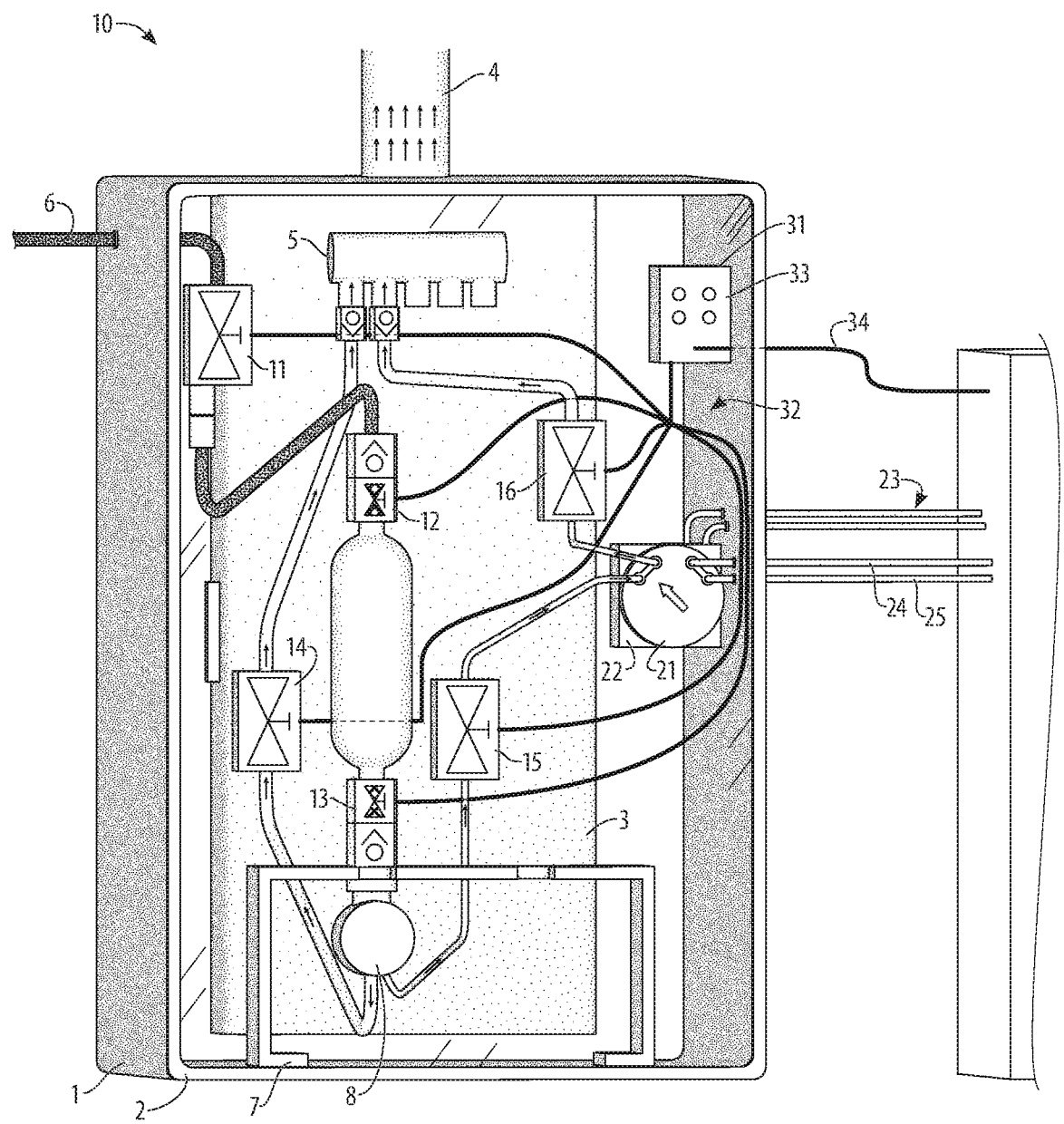
FIG. 6 is a schematic view of the gas-analysis sample injection system of the invention in use at a first step of operation.

Referring to FIG. 6, in an initial, first phase of operation, a standard gas-sample cylinder is mounted between the sample-cylinder inflow valve 12 and sample-cylinder outflow valve 13. The carrier gas regulating valve 11 is opened to allow carrier gas at a regulated pressure into the system. The filter vent valve 14, sample transfer valve 15, and injector-valve vent valve 16 remain open, and the sample injector valve 21 remains closed, as when at rest, to ensure any extraneous air or gas is drawn away into the cabinet vent 3.

Figure 7:
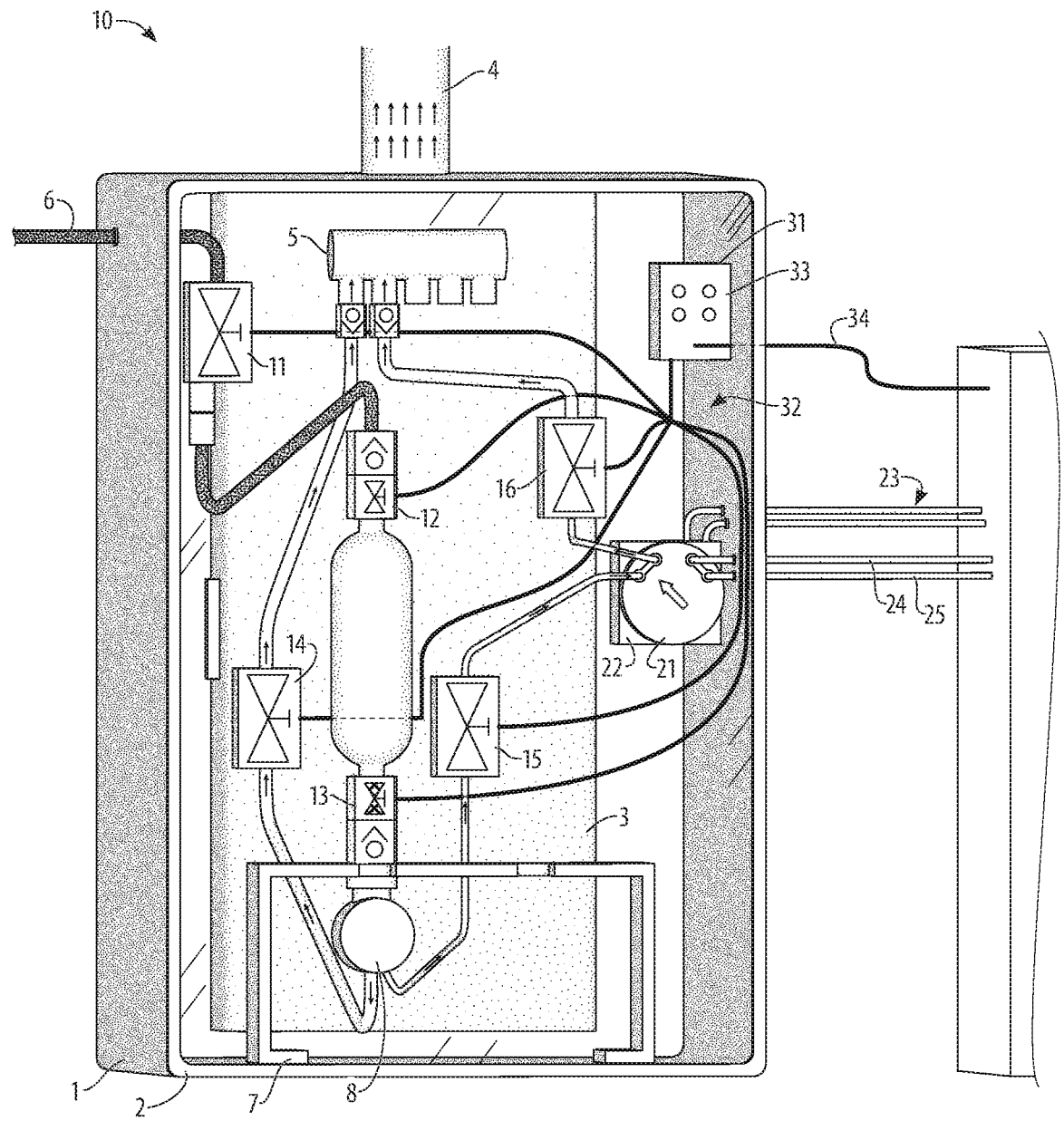
FIG. 7 is a schematic view of the gas-analysis sample injection system of the invention in use at a second step of operation.

Referring to FIG. 7, in a second phase of operation, the sample-cylinder inflow valve 12 is opened to allow entry of carrier gas into the gas-sample cylinder, bringing the gas-sample cylinder up to a regulated pressure. The other valves remain as before, with the negative pressure of the cabinet vent 3 still being applied to draw away any extraneous air or gas, including any inadvertently leaked gasses.

Figure 8:
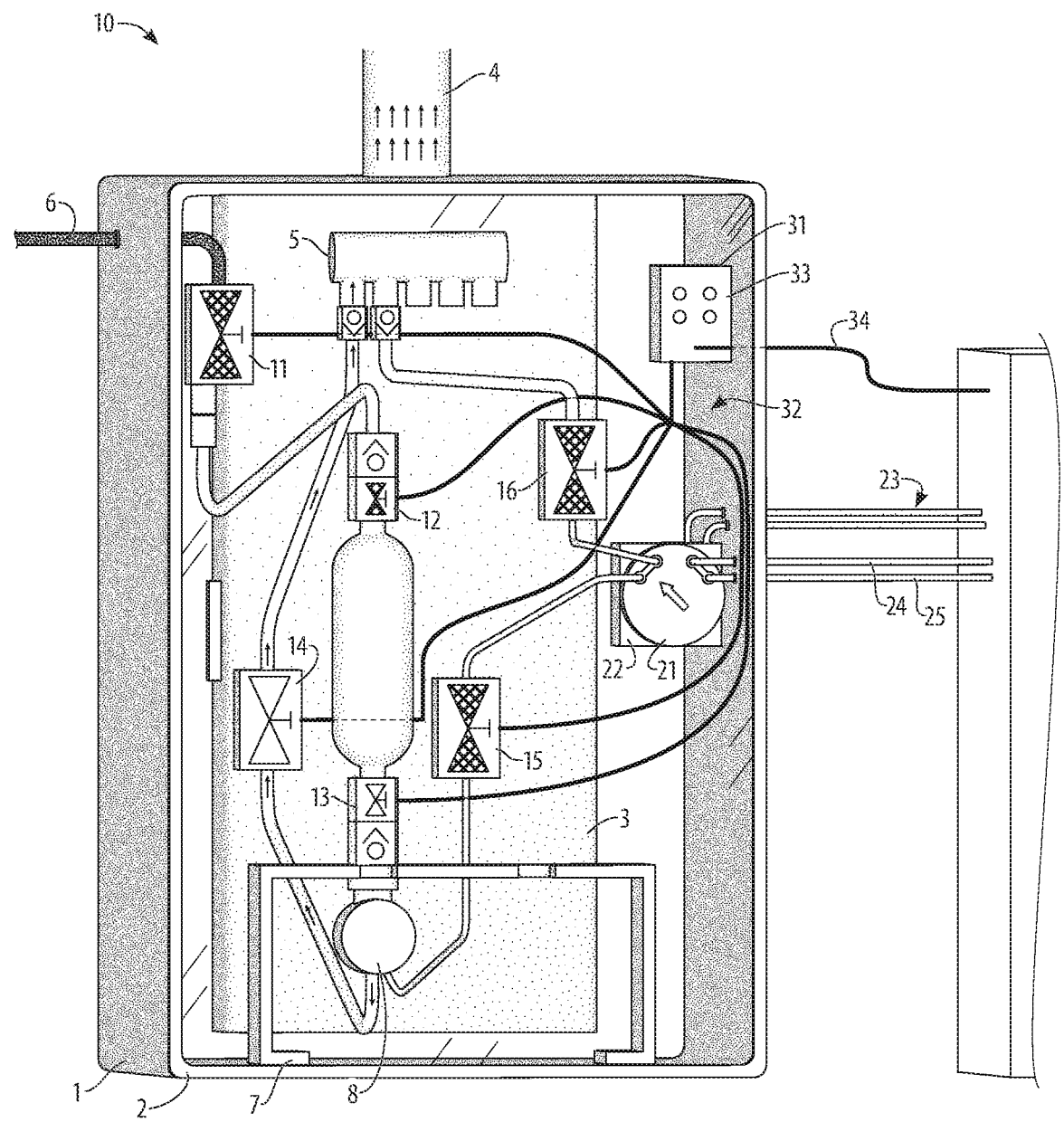
FIG. 8 is a schematic view of the gas-analysis sample injection system of the invention in use at a third step of operation.

Referring to FIG. 8, in a third phase of operation, the sample-cylinder outflow valve 13 is opened to allow the sample gas, mixed with carrier gas, to flow, at regulated pressure, into the sample filter housing 8. The carrier gas regulating valve 11 and sample-cylinder inflow valve 12 are optionally closed to further ensure against leakage or back-flow. The sample filter housing 8 accommodates a filter or filter pack through which the sample gas passes. The placement and configuration of the sample filter housing 8 allows easy access for an operator to inspect or change the filters. As treated above, a negative pressure is applied to the sample filter housing 8 during the at-rest, first, and second phases of operation in order to draw away any extraneous gas that might remain from a previous run. Generally, simultaneously with the opening of the sample-cylinder outflow valve 13, the sample transfer valve 15 is closed, blocking the flow of sample gas toward the sample injector valve 21. When the sample-cylinder outflow valve 13 is opened the filter vent valve 14 remains open momentarily, and the first-exiting portion of sample gas, blocked by the closed sample transfer valve 15, is purged through the open filter vent valve 14, further carrying away any extraneous air or gas. Optionally the injector-valve vent valve 16 is also closed.

Figure 9:
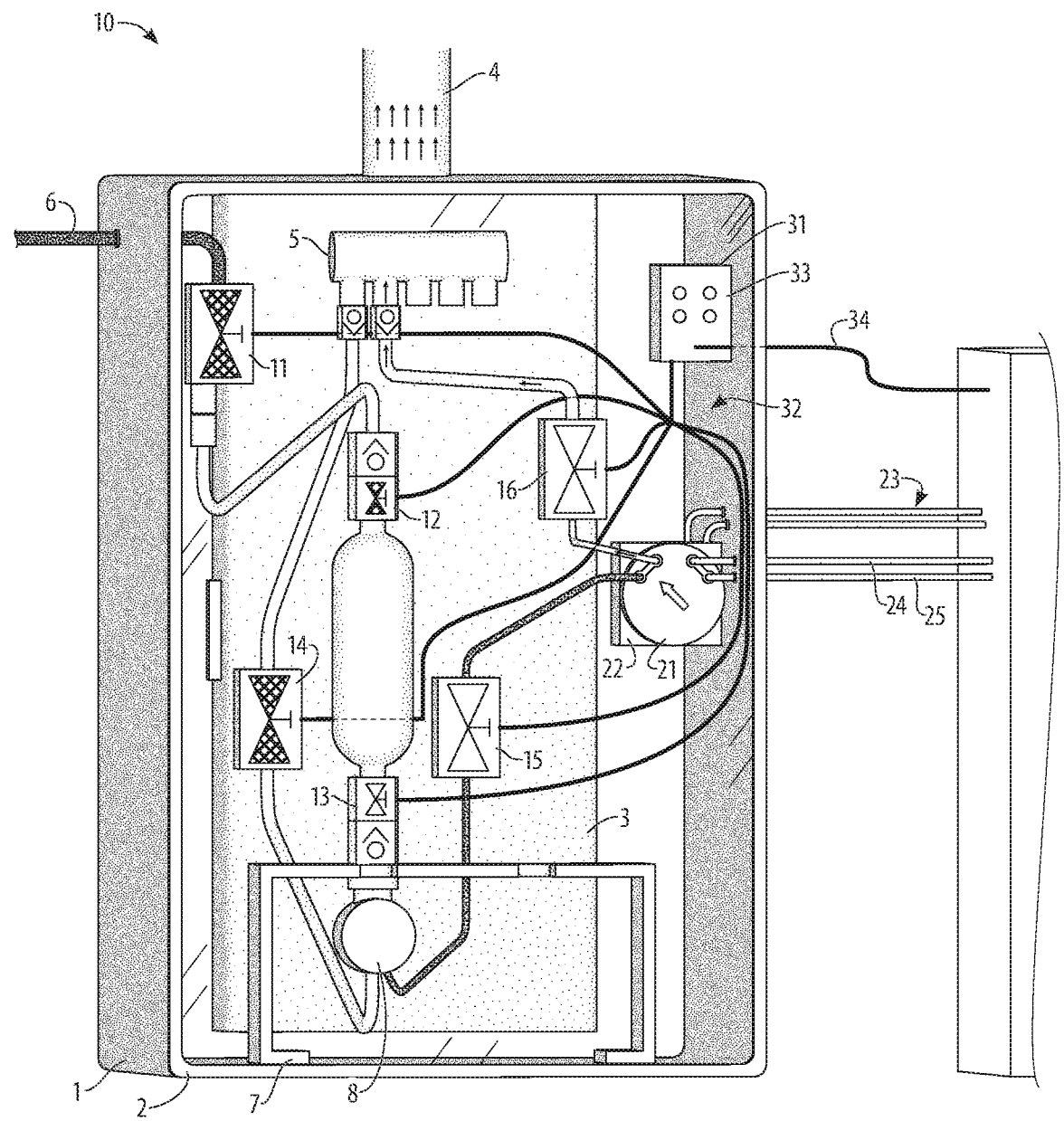
FIG. 9 is a schematic view of the gas-analysis sample injection system of the invention in use at a fourth step of operation.

Referring to FIG. 9, in a fourth phase of operation, the filter vent valve 14 is closed after the purging of the first-exiting portion of sample gas, and the sample transfer valve 15 and injector-valve vent valve 16 are opened, allowing the flow of sample gas into the sample injector valve 21. The injector-valve vent valve 16 is left open momentarily, and the first-arriving portion of sample gas is purged into the cabinet vent 3.

Figure 10:
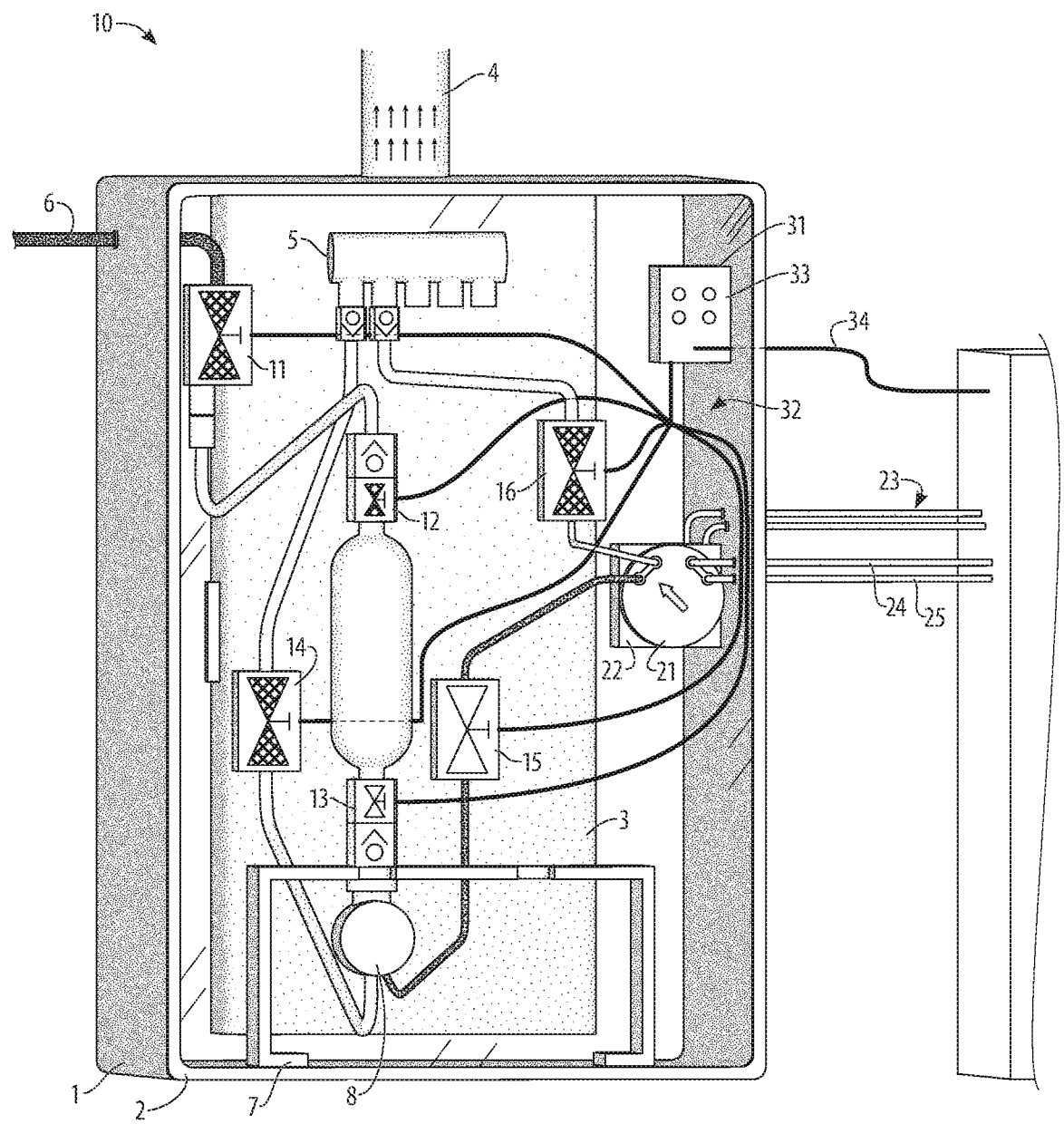
FIG. 10 is a schematic view of the gas-analysis sample injection system of the invention in use at a fifth step of operation.

Referring to FIG. 10, in a fifth phase of operation, the injector-valve vent valve 16 is closed after being left open momentarily in order to purge a portion of the sample gas. The sample gas within the sample injector valve 21 comes up to the regulated pressure, causing a calibrated amount of sample gas to be contained within the transfer chamber of the sample injector valve 21.

Figure 11:
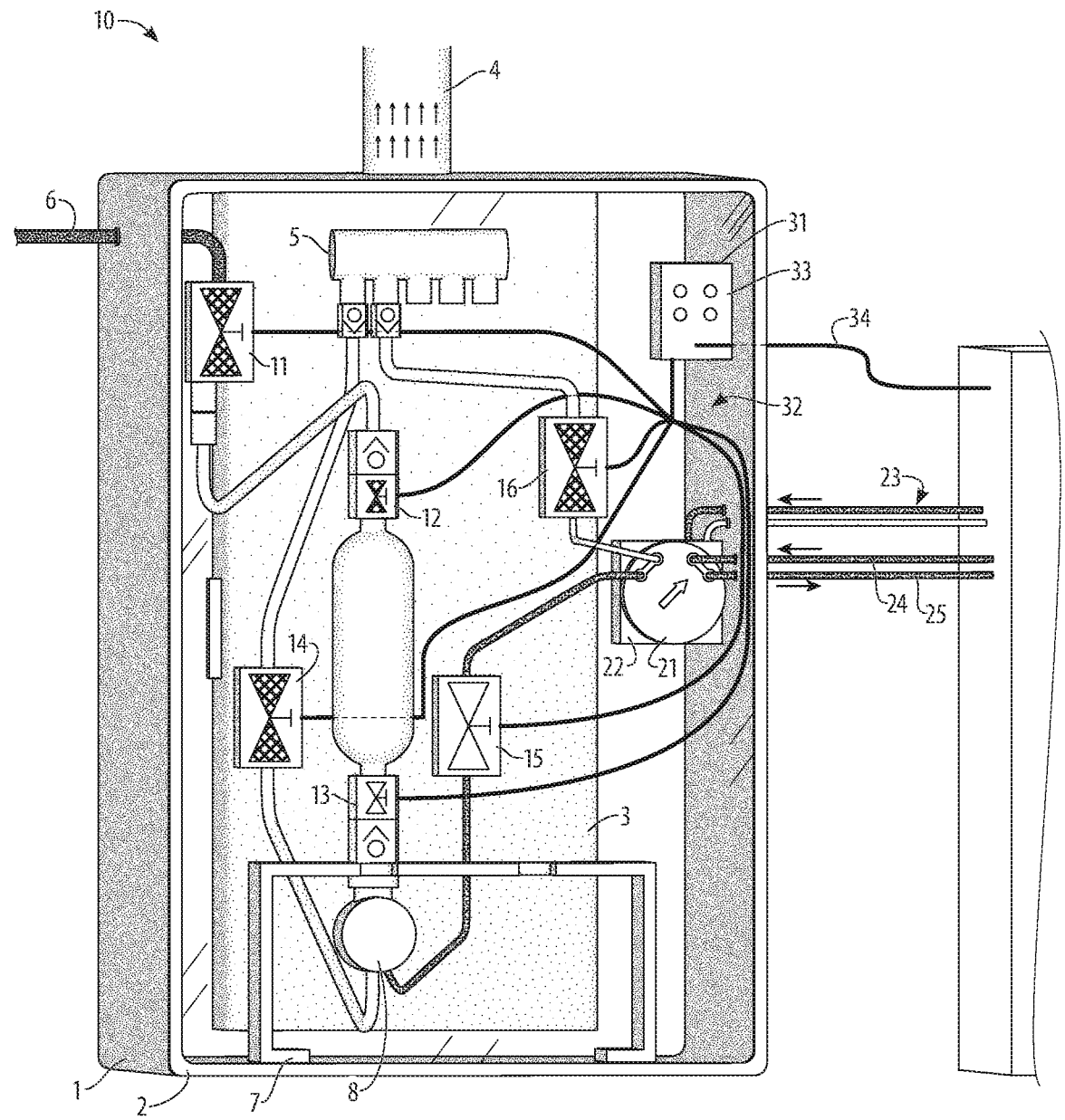
FIG. 11 is a schematic view of the gas-analysis sample injection system of the invention in use at a sixth step of operation.

Referring to FIG. 11, in a sixth phase of operation, the sample injector valve 21 is opened by the injector-valve actuator 22 under the control of the analyzer via the actuator control lines 23, as treated above. Opening of the sample injector valve 21 moves the transfer chamber into alignment so that pressurized carrier gas sent by the analyzer via the sample-injection inflow line 24 carries the sample gas in the transfer chamber into the analyzer via the sample-injection outflow line 25. Analysis of the sample gas is then performed by the analyzer. Optionally, if analysis of multiple consecutive samples of the same sample gas is desired, the sample injector valve 21 can be cycled between the closed and opened state, because the flow of sample gas at regulated pressure remains available during this phase.

Figure 12:
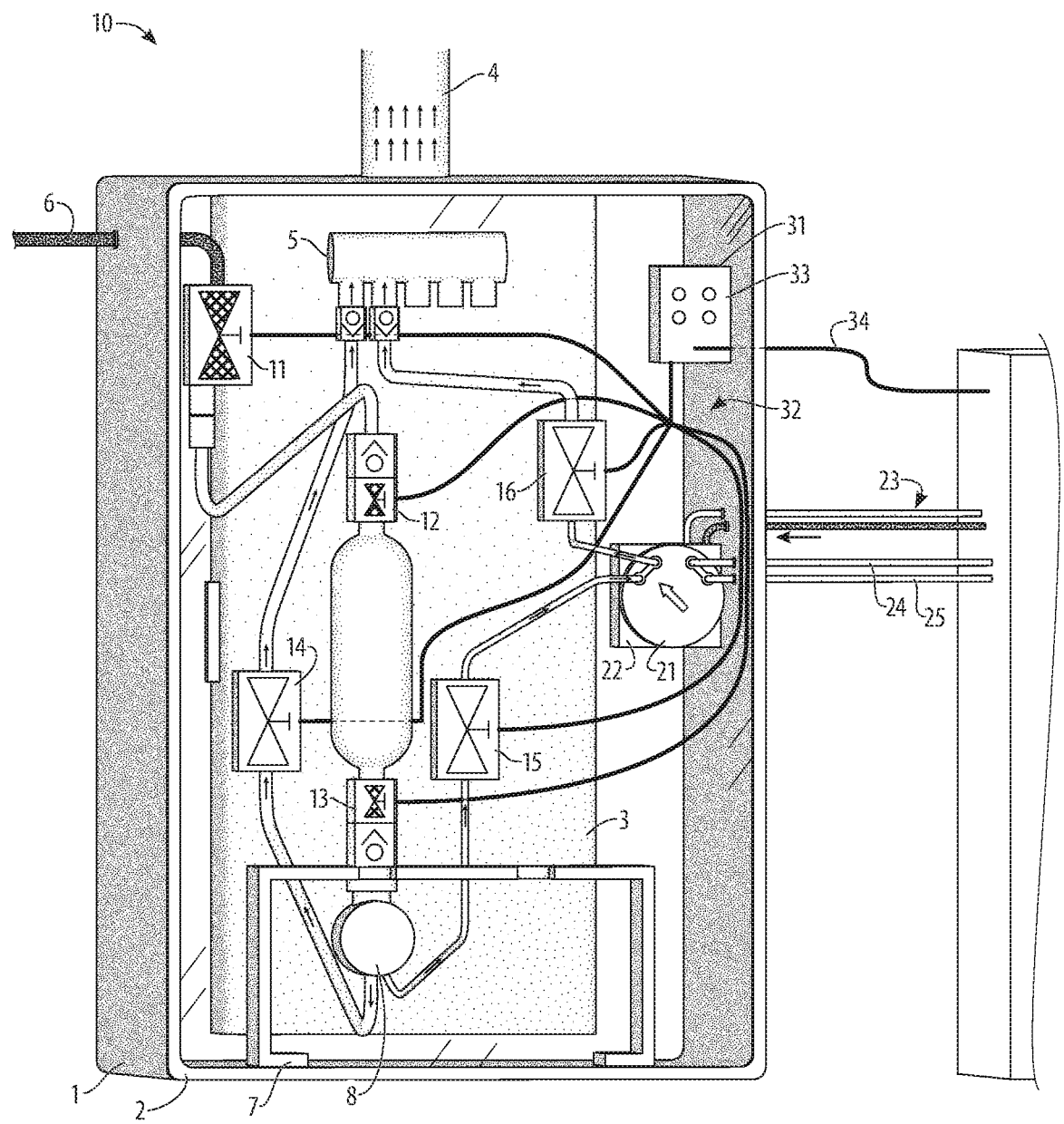
FIG. 12 is a schematic view of the gas-analysis sample injection system of the invention in use at a seventh step of operation.

Referring to FIG. 12, in a seventh and final phase of operation, the sample injector valve 21 is returned to a closed position by the injector-valve actuator 22 under control of the analyzer via the actuator control lines 23. The sample-cylinder outflow valve 13 is closed in preparation for removal of the gas-sample cylinder. The sample transfer valve 15 remains open and the filter vent valve 14 and injector-valve vent valve 16 are opened, causing the negative pressure of the cabinet vent 3 to be re-applied throughout the system and carrying away any remaining extraneous gas. After the gas-sample cylinder is removed, the gas-analysis sample injection system 10 returns to its at-rest state.

Many other changes and modifications can be made in the system and method of the present invention without departing from the spirit thereof. I therefore pray that my rights to the present invention be limited only by the scope of the appended claims.

I claim:

1. A gas-analysis sample injection method comprising:
   (i) providing a gas-analysis sample injection system comprising:
      (a) a cabinet having a door, adapted to safely contain emitted gas;
      (b) a cabinet vent mounted within said cabinet, adapted to vent gasses emitted during operation;
      (c) a vent exhaust extending from said cabinet, adapted to exhaust gas from said cabinet vent;
      (d) a vent manifold extending from said cabinet vent within said cabinet, adapted to provide quick connection for a plurality of hoses;
      (e) a carrier-gas supply adapted to supply pressurized carrier gas to the interior of said cabinet;
      (f) a sample cylinder support bracket mounted within said cabinet, adapted to hold in place at least one gas-sample cylinder;
      (g) a sample filter housing mounted upon said sample cylinder support bracket in a position accessible from the position of said door, adapted to accommodate and facilitate changing of sample filters;
      (h) a carrier gas regulating valve mounted within said cabinet at said carrier gas supply, adapted to control the flow and pressure of carrier gas;
      (i) a sample injector valve mounted within said cabinet, adapted to supply a calibrated amount of gas to the analyzer, through a sample-injection outflow line, moved by additional carrier gas supplied by the analyzer through a sample-injection inflow line;
      (j) a sample-cylinder inflow valve connected by hose to said carrier gas regulating valve, adapted to being removably mounted to a gas-sample cylinder, and adapted to control flow of carrier gas into the gas-sample cylinder;
      (k) a sample-cylinder outflow valve adapted to being removably mounted to a gas-sample cylinder, and adapted to control flow of gas from the gas-sample cylinder into said sample filter housing;
      (l) a filter vent valve connected by hoses to said sample filter housing and said vent manifold, adapted to allow a momentary flow of gas from said sample filter housing to said vent manifold;
      (m) a sample transfer valve connected by hoses to said sample filter housing and said sample injector valve, adapted to control flow of gas from said sample filter housing to said sample injector valve;
      (n) an injector-valve vent valve connected by hoses to said sample injector valve and said vent manifold, adapted to allow a momentary flow of gas from said sample injector valve to said vent manifold;
      (o) an injector-valve actuator connected to said sample injector valve, adapted to activate said sample injector valve under control of actuator control lines in turn controlled by the analyzer;
      (p) a valve controller adapted to control the operation of said carrier gas regulating valve, sample-cylinder inflow valve, sample-cylinder outflow valve, filter vent valve, sample transfer valve, and injector-valve vent valve via valve-control lines; and (q) a control panel attached to said valve controller, adapted to provide an operator interface;

(ii) providing venting through said vent manifold, said cabinet vent, and said vent exhaust when said gas-analysis sample injection system is not in active use by opening said filter vent valve, said sample transfer valve, and said injector-valve vent valve, with said sample injector valve closed;

(iii) initiating use by opening said door, mounting a gas-sample cylinder between said sample-cylinder inflow valve and said sample-cylinder outflow valve, closing said door, and activating said valve controller;

(iv) using said gas-analysis sample injection system where, under control of said valve controller, said carrier gas regulating valve and said sample-cylinder inflow valve are opened to provide pressurization of the gas-sample cylinder with carrier gas, said sample transfer valve is closed, said sample-cylinder outflow valve is opened to allow flow of sample gas into said sample filter housing, said filter vent valve is left open momentarily to allow venting from said sample filter housing and is then closed, said sample transfer valve is opened to allow flow of sample gas from said sample filter housing to said sample injector valve, said injector-valve vent valve is left open momentarily to allow venting from said sample injector valve and is then closed, said sample injector valve is opened by said injector-valve actuator under control from the analyzer over said actuator control lines, sample gas is transferred to the analyzer through said sample-injection outflow line on a flow of carrier gas provided by the analyzer through said sample-injection inflow line, said sample injector valve is closed under control from the analyzer over said actuator control lines, and said sample-cylinder inflow valve and said sample-cylinder outflow valve are closed; and (v) removing the gas-sample cylinder.

2. The gas-analysis sample injection method of claim 1, where said gas-analysis sample injection system further comprises an analyzer communication line adapted to allow communication with the analyzer.

3. The gas-analysis sample injection method of claim 1, where said gas-analysis sample injection system further comprises a controller remote-command unit adapted to provide an operator interface with said valve controller from outside said cabinet.

4. The gas-analysis sample injection method of claim 1, where said gas-analysis sample injection system further comprises a controller remote-command unit adapted to provide a wireless operator interface with said valve controller from outside said cabinet.

5. The gas-analysis sample injection method of claim 1, where said sample cylinder support bracket further comprises being adapted to hold in place at least two gas-sample cylinders.

6. The gas-analysis sample injection method of claim 1, where said sample cylinder support bracket further comprises being adapted to hold in place at least three gas-sample cylinders.

7. The gas-analysis sample injection method of claim 1, where said control panel further comprises being located on the exterior of said cabinet.

8. The gas-analysis sample injection method of claim 1, where said control panel further comprises being located on said door.

9. The gas-analysis sample injection method of claim 1, where said cabinet and said door further comprise being adapted to withstand an explosive force.

* * * * *